United States Patent [19]
Shemesh et al.

[11] Patent Number: 5,853,397
[45] Date of Patent: Dec. 29, 1998

[54] MEDICAL INFUSION APPARATUS INCLUDING SAFETY VALVE

[75] Inventors: Eli Shemesh, Ashdod; Swi Barak, Caesaria; Haim Raz, Rehovot, all of Israel

[73] Assignee: Migada, Inc., N.J.

[21] Appl. No.: 663,065

[22] PCT Filed: Dec. 12, 1994

[86] PCT No.: PCT/US94/14334

§ 371 Date: Sep. 13, 1996

§ 102(e) Date: Sep. 13, 1996

[87] PCT Pub. No.: WO95/16480

PCT Pub. Date: Jun. 22, 1995

[30] Foreign Application Priority Data

Dec. 13, 1993 [IL] Israel ........................................ 108004
Jul. 3, 1994 [IL] Israel ........................................ 110198

[51] Int. Cl.⁶ .................................................... A61M 5/00
[52] U.S. Cl. ............................................................ 604/247
[58] Field of Search .................................. 604/276, 247, 604/248, 249, 257

[56] References Cited

U.S. PATENT DOCUMENTS

| Re. 34,243 | 5/1993 | Gerber | 604/247 |
|---|---|---|---|
| 3,982,534 | 9/1976 | Bulkman | 604/246 |
| 4,244,379 | 1/1981 | Smith | 604/247 |
| 4,346,704 | 8/1982 | Kulle | 604/247 |
| 4,527,588 | 7/1985 | Tseo | 137/365 |
| 4,657,536 | 4/1987 | Dorman | 604/247 |
| 4,758,224 | 7/1988 | Siposs | 604/247 |
| 4,895,346 | 1/1990 | Steigerwald | 604/247 |
| 5,098,396 | 3/1992 | Taylor | 604/246 |
| 5,158,539 | 10/1992 | Kolff et al. | 604/31 |
| 5,169,393 | 12/1992 | Moorehead | 604/257 |
| 5,211,201 | 5/1993 | Kamen et al. | 604/122 |
| 5,300,044 | 4/1994 | Classey | 604/250 |
| 5,356,379 | 10/1994 | Vaillancourt | 604/80 |
| 5,401,255 | 3/1995 | Sutherland | 604/247 |

*Primary Examiner*—Max Hindenburg
*Attorney, Agent, or Firm*—Ladas & Parry

[57] ABSTRACT

Medical infusion apparatus includes a container for a liquid to be infused, tubing leading from the container to the subject to receive an infusion, a pump for pumping the infusion liquid via the tubing to the subject, and a safety valve connected in the tubing between the pump and the subject. The safety valve is normally closed to prevent free-flow of the liquid from the container, but is automatically opened when a predetermined minimum pressure is applied to the liquid by the pump. The safety valve is also manually deformable to open the valve and to permit priming the apparatus.

4 Claims, 6 Drawing Sheets

MEDICAL INFUSION APPARATUS INCLUDING SAFETY VALVE

The present invention relates to medical infusion apparatus such as used for administering an infusion liquid intravenously to a subject. The invention relates in particular to a safety valve included in such infusion apparatus.

For many years, infusion liquids have been administered to subjects intravenously by gravity feeding the infusion liquid from a container, e.g., a plastic bag, supported above the subject. More recently, such infusion apparatus have included pumps, particularly peristaltic pumps, which provide better control of the infusion rate. The use of such pumps, however, has created a dangerous situation which can occur before the pump has been connected into the infusion tubing or after it has been disconnected therefrom. Thus, in either of such situations, the attendant may accidentally leave the infusion tubing connected to the patient and not be aware that the patient is receiving infusion liquid by gravity feed from the infusion bag. This can be harmful, or even fatal, to the patient. Many pump constructions for infusion apparatus are provided with special protective arrangements to preclude this possible danger, but the danger still exists when infusion apparatus is used with a pump not provided with such special protection.

An object of the present invention is to provide medical infusion apparatus that includes protection against this possible danger even when the apparatus is used with a pump not provided with such a protective feature. Another object of the invention is to provide medical infusion apparatus which can be conveniently primed, i.e., purged of all air in the tubing, before the apparatus is connected to the patient.

According to the present invention, there is provided medical infusion apparatus, comprising: a container for a liquid to be infused; tubing leading from the container to the subject to receive an infusion; a pump for pumping the infusion liquid via the tubing to the subject; and a safety valve connected in the tubing between the pump and the subject; the safety valve being normally closed to prevent free-flow of the liquid from the container but being automatically opened when a predetermined minimum pressure is applied to the liquid by the pump, the safety valve also being manually deformable to open the valve and to permit priming of the apparatus.

Several embodiments of the invention are described below for purposes of example.

Medical infusion apparatus equipped with such a safety valve normally blocks the flow of the infusion liquid, thereby preventing infusion liquid from being gravity-fed to the patient should the pump be disconnected. However, such a safety valve is automatically opened by a predetermined minimum liquid pressure as applied by the pump. It may also be manually opened by manually deforming (e.g., squeezing, bending or twisting) it to permit priming the apparatus. Such apparatus thus provides protection against the above-mentioned danger of inadvertently feeding infusion liquid to the patient when the pump is disconnected, and also enables the apparatus to be primed in a convenient manner.

FIG. 1 pictorially illustrates one form of medical infusion apparatus in accordance with the present invention;

Figure 15:
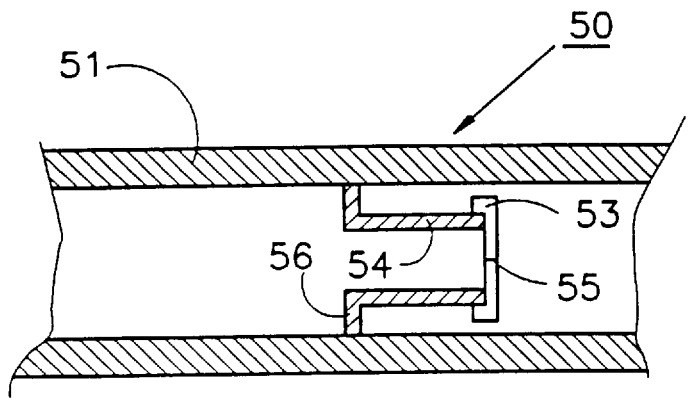
Figure 16:
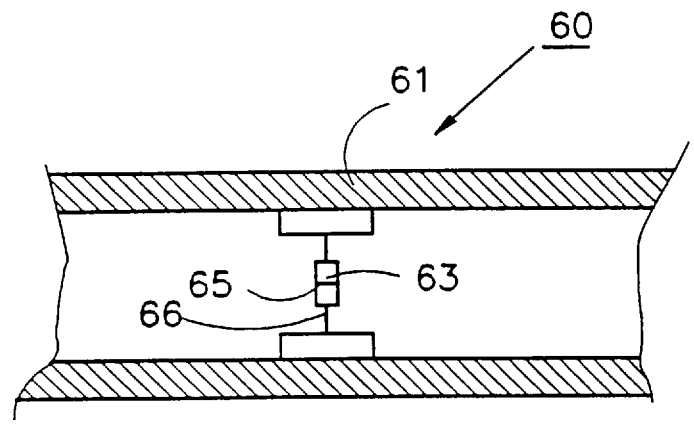
Figure 16A:
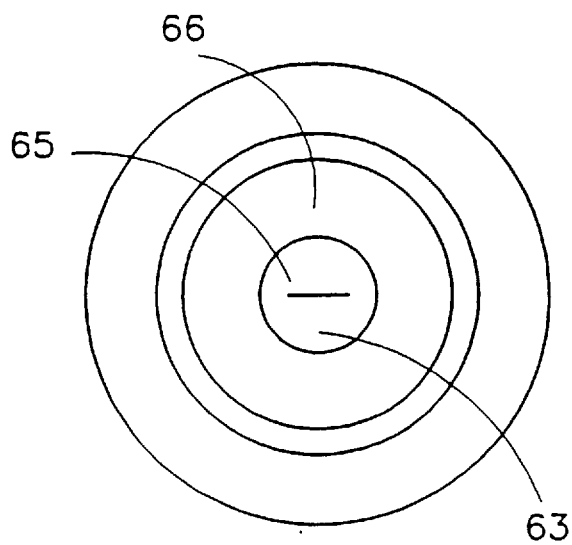
Figure 17:
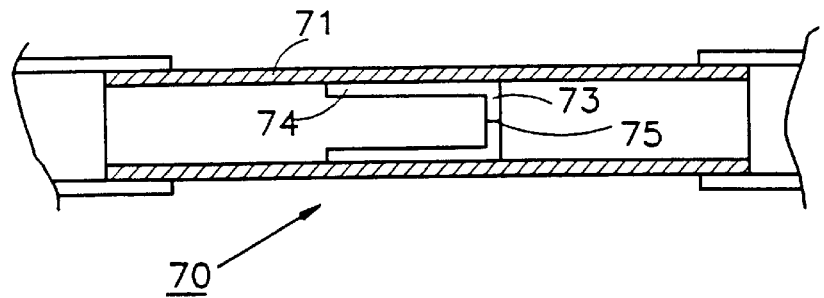
Figure 18:
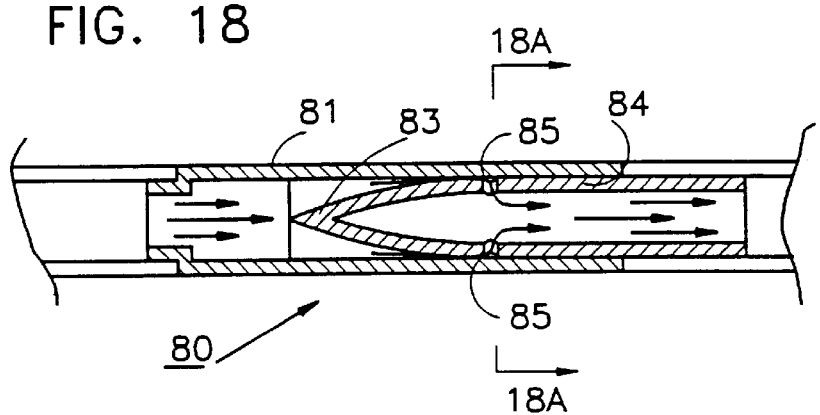
Figure 18A:
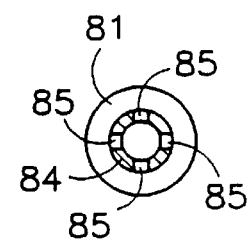

and FIGS. 15, 16, 16A, 17, 18, 18A and 19 illustrate still further constructions of safety valves that may be used, FIG. 16a being a front view of the construction of FIG. 16, and FIG. 18a being a sectional view along line 18a–18a of FIG. 18.

Figure 1:
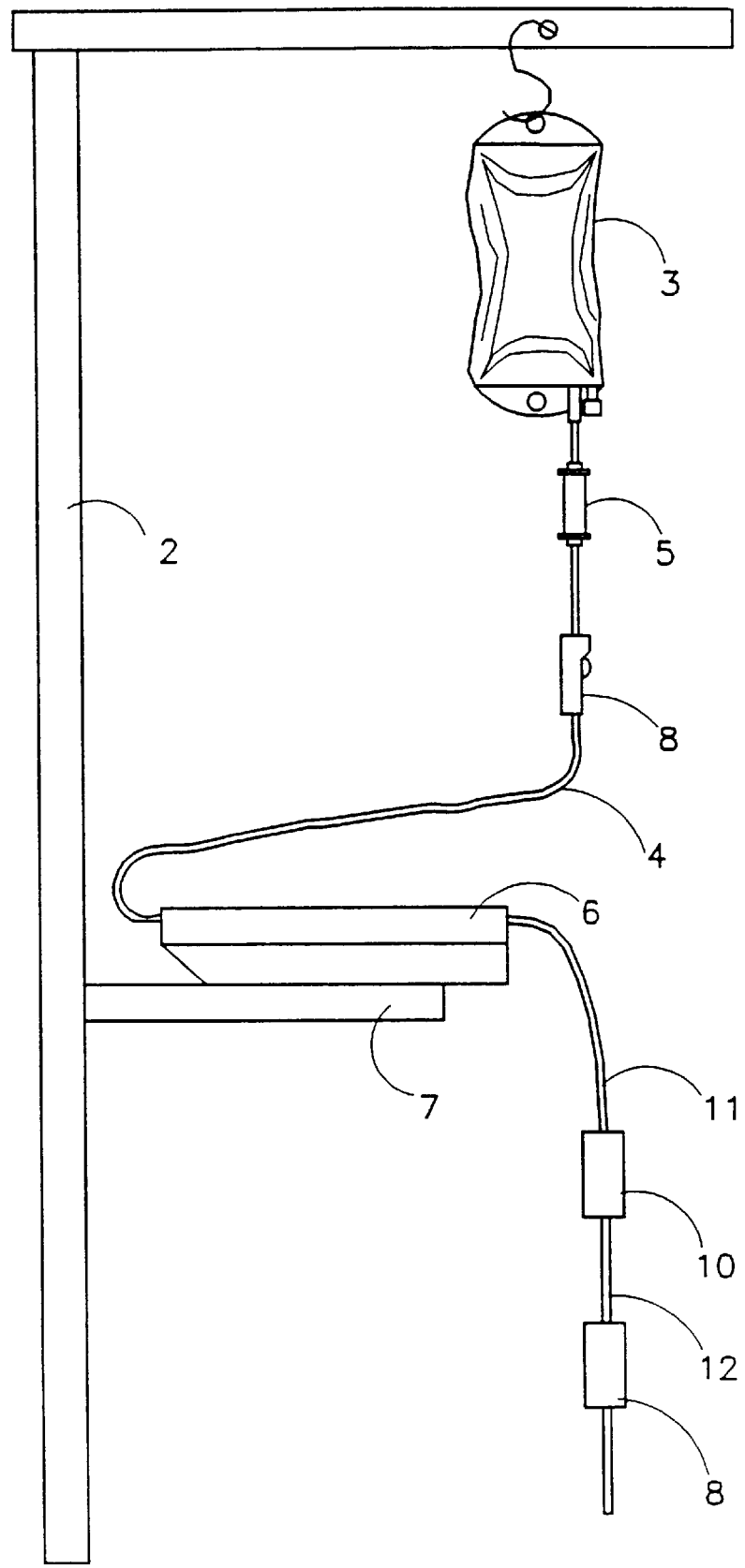
Figure 2:
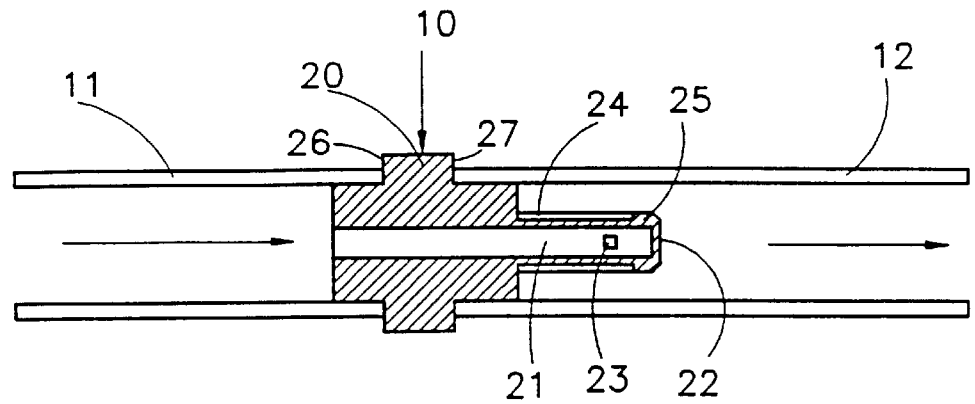
FIG. 2 is a longitudinal sectional view illustrating one form of safety valve that may be used with the apparatus in accordance with the present invention.
Figure 3:
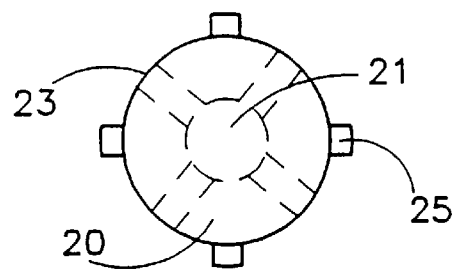
FIGS. 3, 4 and 5 are end views illustrating the safety valve of FIG. 2, respectively, without the elastomeric sleeve, with the elastomeric sleeve in its closed condition, and with the elastomeric sleeve in its open condition.
Figure 4:
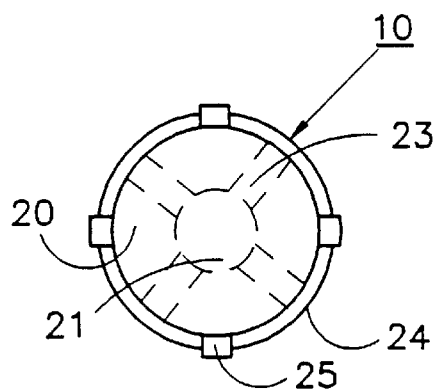

The infusion apparatus illustrated in FIG. 1 includes a holder 2 for holding a container 3, such as a plastic bag, for the infusion liquid at a height above that of the subject to receive the infusion. The infusion is fed via tubing 4 connected at one end to the infusion container 3, and including a needle or luer connector (not shown) at the opposite end for administering the infusion liquid intravenously to the subject. The illustrated apparatus further includes a drip chamber 5, a pump (e.g., a peristaltic pump) 6 supported on a support 7, and optionally, roller clamps 8 that may be used for controlling the flow of the infusion liquid to the subject.

As indicated earlier, there is a danger that, either before pump 6 is connected to the infusion tubing 4 or after it has been disconnected, the attendant will not be aware that the infusion tubing is still attached to the subject so that the subject still receives infusion liquid by gravity feed from the infusion container 3. When the pump 6 is not connected, the attendant should shut-off the flow of the infusion liquid by a roller clamp 8, but the attendant may inadvertently not do this and at the same time not be aware that the subject is receiving infusion liquid by gravity feed. As indicated above, this can be extremely harmful and possibly even fatal, to the patient.

To reduce or eliminate this danger, the infusion tubing 4 illustrated in FIG. 1 further includes a safety valve, generally designated 10. Safety valve 10 is connected by tubing 11 on one side to the pump 6, and on the opposite side to tubing 12 leading to the patient. The safety valve is normally closed so that it automatically blocks the flow of the infusion liquid through the tubing 12; but automatically opens when a predetermined liquid pressure is applied by the infusion liquid to the safety valve. This predetermined pressure is larger than that of the pressure head but smaller than that produced by pump 6 so that the safety valve is automatically closed when the pump is not connected, but automatically opens as soon as the pump is connected and operated.

Preferably, safety valve 10 should prevent free flow at pressures that are less than 0.2 atm, and should allow a maximum pressure drop of approximately 0.4 atm. Pump 6 may provide a maximum pressure of 0.5 atm.

As will be described below, safety valve 10 may also be manually opened by manually squeezing it to permit priming the apparatus, i.e., purging it of air.

FIGS. 2–19 illustrate examples of constructions that the safety valve 10 may have in order to perform the above functions.

Safety valve 10 illustrated in FIGS. 2–5 includes a cannula 20 having an axial passageway 21 starting from one end and closed at the opposite end 22. Cannula 20 is further formed with four radial bores 23 adjacent the closed end 22 and leading from the axial passageway 21 to the outer surface of the cannula. An elastomeric sleeve 24 is applied around the cannula overlying the radial bores 23. The outer surface of the cannula is further formed with a ribbed formation 25 including four circumferentially-spaced ribs, for locating the elastomeric sleeve 24 and preventing it from slipping over the end of the cannula.

One end of cannula 20 is formed with an annular seat 26 for receiving tube 11, and its opposite end is formed with another annular seat 27 for receiving tube 12, whereby the cannula connects together the two tubes 11, 12, with the safety valve in between.

Figure 5:
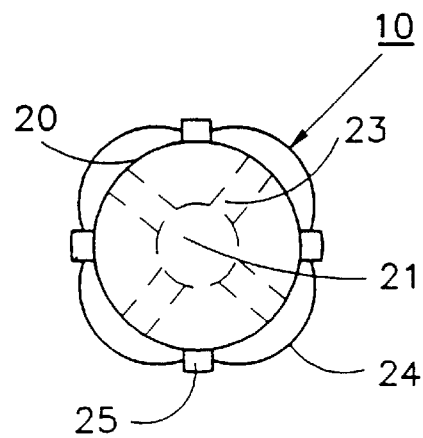

It will thus be seen that the radial bores 23 are normally closed by the elastomeric sleeve 24, thereby blocking the flow from tube 11 to tube 12. However, when a sufficient pressure is applied by the pump 6 (FIG. 1), sleeve 24 deforms, as shown in FIG. 5, to permit fluid flow from tube 11 to tube 12 via passageway 21 and the opened radial bores 23.

It will also be seen that the cannula 20 and the overlying sleeve 24 may be squeezed together to open the radial bores 23 in order to permit manual priming of the apparatus before connecting it to the pump. Thus, squeezing the opposite sides of the sleeve 24 will deform it into an elliptical shape and will cause the portions of the sleeve not engaged by the user's fingers to move outwardly away from the outer surface of the cannula to thereby uncover the respective radial bores 23. This opening of the radial bores to permit manual priming of the apparatus would be further enhanced by making the cannula 20 also deformable by this squeezing pressure.

Preferably, the inner faces of the cannula 20 and the elastomeric sleeve 24 are lubricated with a silicone oil. Medically approved oil for this purpose is available from Dow Corning.

Figure 6:
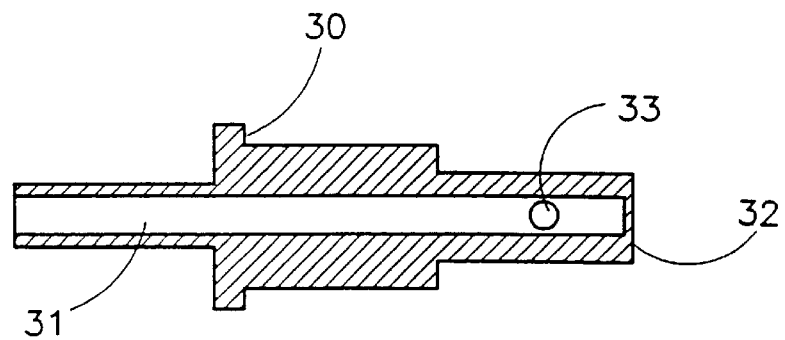
FIG. 6 is a longitudinal sectional view illustrating a modification in the construction of the cannula in the safety valve of FIGS. 2–5.
Figure 7:
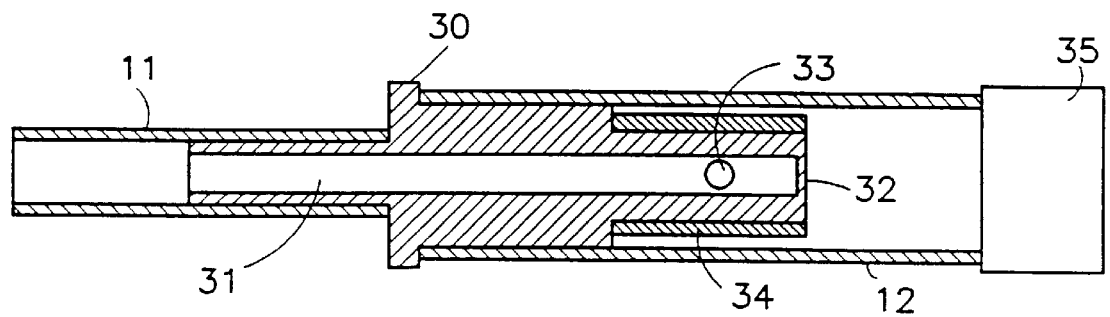
FIG. 7 is a side view illustrating the safety valve of FIG. 6 assembled with the elastomeric sleeve.

FIG. 6 illustrates a modified construction of the cannula which may be used as the safety valve. In this case, the cannula, generally designated 30, is also formed with an actual passageway 31 closed at one end 32 but communicating with four radial bores 33 adjacent to the closed end and leading to the outer surface of the cannula. As shown by FIG. 7, the radial bores 33 are closed by an elastomeric sleeve 34 connected at one end to one part of a luer lock 35, which is matable with the other part of a luer lock (not shown) to which the other tube (12, FIG. 2) is connected.

Figure 8:
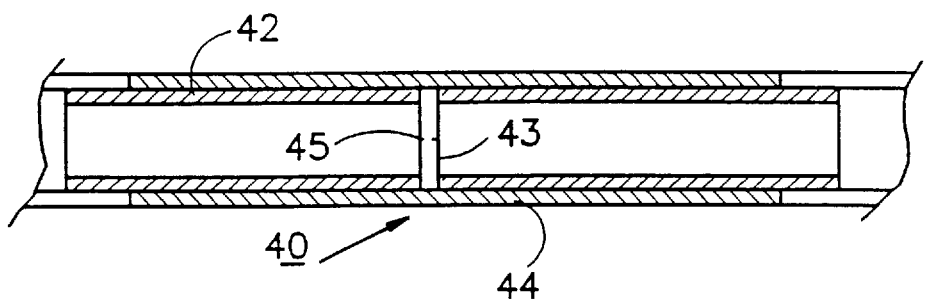
FIG. 8 is a longitudinal sectional view illustrating another form of safety valve that be included in the apparatus of FIG. 1, the safety valve being shown in its normally closed condition.
Figure 9:
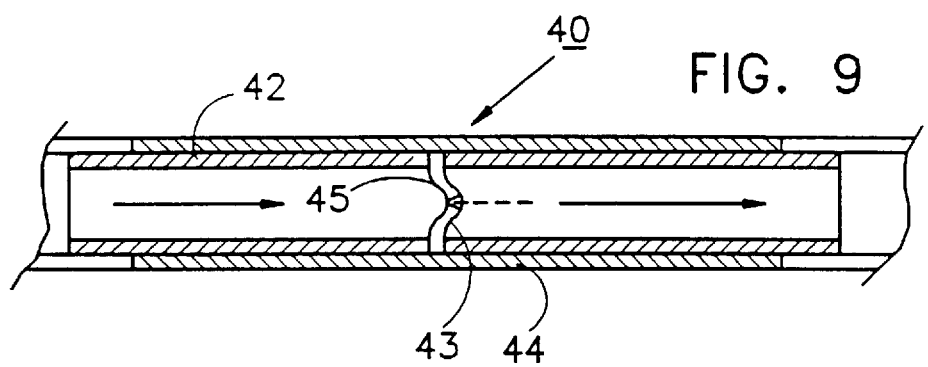
FIG. 9 is a view similar to that of FIG. 8, but showing the safety valve in its open condition.

Safety valve 40 illustrated in FIGS. 8 and 9 includes an inner resilient tube 42 formed with a transverse wall 43, and an outer resilient tube 44. Transverse wall 43 is formed with a slit formation, schematically indicated at 45, which is normally closed to block the liquid flow, but is automatically opened, as shown schematically in FIG. 9, when a predetermined minimum pressure is applied to the liquid or when the tube is manually squeezed.

Figure 10:
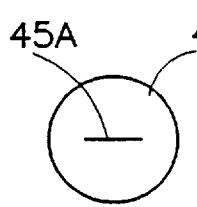
FIGS. 10–14 illustrate various types of slit formations that may be provided.
Figure 11:
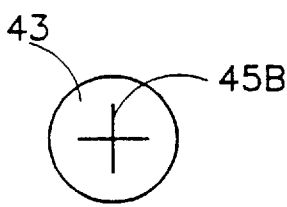
Figure 12:
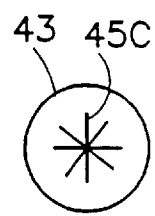
Figure 13:
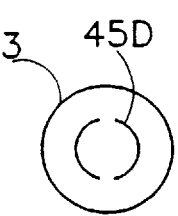
Figure 14:
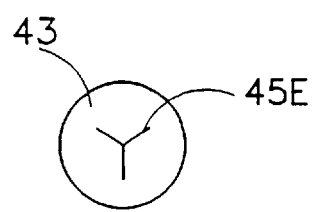

FIGS. 10–14 illustrate examples of slit formations which may be provided in the transverse disc 43. Thus, FIG. 10 illustrates the slit formation 45a in the form of a single linear slit in the central region of the disc 43; in order to open slit 45a manually, finger pressure would be applied on opposite sides of the linear slit 45a and in alignment with it. FIGS. 11 and 12 illustrate the slit formation, shown at 45b and 45c, respectively, in the form of a plurality of crossing linear slits in the central region of the disc; FIG. 13 illustrates the slit formation 45d in the form of two curved slits in the central region of the disc 43; and FIG. 14 illustrates the slit formation 45e in the form of three, Y-connected slits.

FIG. 15 illustrates the safety valve, therein designated 50, also including a resilient tube 51. In this case, however, the transversely extending wall is the end wall 53 of an inner resilient cup 54 received within resilient tube 51. End wall 53 of cup 54 is formed with the slit formation 55, which may take any of the configurations as described above. Cup 54 is spaced from the inner surface of resilient tube 51 by an annular ring 56.

FIG. 16 illustrates a construction for the safety valve, therein designated 60, which also includes a resilient tube 61 and a transversely-extending wall 63 normally blocking the flow but formed with a slit formation 65 which may be opened for permitting the flow as described above. In this case, however, the transverse wall 63 is in the form of a membrane having an annular region 66 of reduced thickness around the central region formed with the slit formation 65.

FIG. 17 illustrates a construction of safety valve, therein designated 70, similar to that of FIG. 15, namely including a resilient tube 71, and an inner cup 74 having an end wall 73 formed with the slit formation 75 and bonded to the inner face of the outer resilient tube 71. Whereas the cup 54 in FIG. 15 is bonded to the outer tube spaced from its inner surface, in FIG. 17 the cup 74 is bonded with its outer surface in direct contact with the inner surface of the outer tube 71.

FIGS. 18 and 18a illustrate a slightly different construction for the safety valve, therein designated 80. This construction also includes an outer resilient tube 81 which is normally closed by a transverse wall extending across the resilient tube and including an opening which is normally closed, but which may be opened as described above. In this case, however, the transverse wall is the closed end 83 of a second resilient tube 84 received within resilient tube 81, and the openings are in the form of a plurality of holes 85 formed in tube 84 adjacent its closed end 83 such that these openings are normally closed by the outer resilient tube 81. However, when the outer tube 81 is subjected to fluid pressure from the pump, or pinched, the two tubes 81, 84 are so deformed that some of the holes 85 would be opened.

Figure 19:
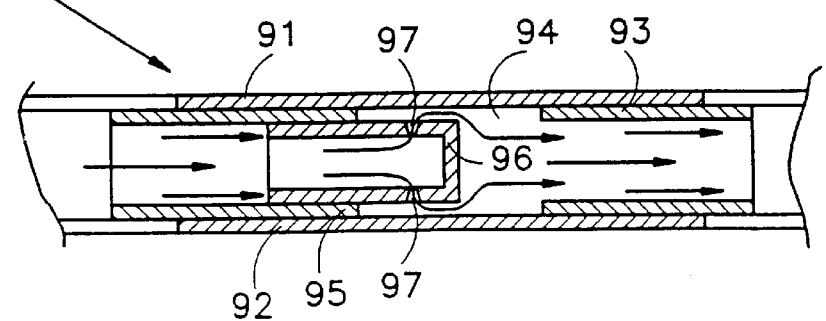

FIG. 19 illustrates a still further variation wherein the safety valve, therein designated 90, also includes an outer resilient tube 91. This construction, however, includes an intermediate tube 92, 93 at each of the opposite ends of the safety valve 90 and spaced from each other within the valve to define an annular space 94. A resilient cup 95 is bonded to the inner face of one of the tubes 92 in alignment with the annular space 94. The resilient cup 95 is formed with a closed end wall 96 to normally block the flow. Cup 95 is further formed with a slit formation 97 at spaced points around its circumference adjacent to its end wall 96 closing that end of the tube.

It will be seen that the construction illustrated in FIG. 19 also operates as described earlier. Thus, in the normal condition of the safety valve, its slits 97 are closed so as to block the flow, but the slits are automatically opened by a liquid pressure greater than a predetermined minimum, and also by manually pinching the outer tube 91 when it is desired to prime the system.

We claim:

1. Medical infusion apparatus, comprising: a container for a liquid to be infused; tubing leading from the container to the subject to receive an infusion; a pump for pumping the infusion liquid via said tubing to the subject; and a safety valve connected in said tubing between said pump and the subject; said safety valve being normally closed to prevent free-flow of the liquid from the container but being automatically opened when a predetermined minimum pressure is applied to the liquid by said pump, wherein said safety valve comprises: a cannula having an axial passageway from one end of the cannula but closed at an opposite end, and a radial bare adjacent said opposite end leading from said axial passageway to an outer surface of the cannula; and an elastomeric sleeve around the cannula and overlying and normally closing said radial bore, wherein said safety valve is adapted for external manual deformation to open the valve and to permit priming of the apparatus.

2. The apparatus according to claim 1, wherein said cannula includes an annular seat at both ends for receiving said tubing in order to connect two sections of said tubing together with the safety valve in between.

3. The apparatus according to claim 1, wherein the outer surface of said opposite end of the cannula is formed with a ribbed formation for locating said elastomeric sleeve.

4. Medical infusion apparatus, comprising: a container for a liquid to be infused; tubing leading from the container to the subject to receive an infusion; a pump for pumping the infusion liquid via said tubing to the subject; and a safety valve connected in said tubing between said pump and the subject; said safety valve being normally closed to prevent free-flow of the liquid from the container but being automatically opened when a predetermined minimum pressure is applied to the liquid by said pump; said safety valve also being manually deformable to open the valve and to permit priming of the apparatus, wherein said safety valve comprises: a cannula having an axial passageway from one end of the cannula but closed at an opposite end, and a radial bore adjacent said opposite end leading from said axial passageway to the outer surface of the cannula; and an elastomeric sleeve around the cannula and overlying and normally closing said radial bore, further including a lubricant between the outer surface of the cannula and the inner surface of the elastomeric sleeve.

* * * * *

UNITED STATES PATENT AND TRADEMARK OFFICE
CERTIFICATE OF CORRRECTION

Page 1 of 2

PATENT NO. : 5,853,397
DATED : December 29, 1998
INVENTOR(S) : Eli Shemesh, et. al.

It is certified that error appears in the above-identified patent and that said Letters Patent is hereby corrected as shown below:

Title page, item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 7 | 2 | 2 | 7 | 3 | 1 | 2/1988 | Vailancourt | | | |
| | | | | | | | | | | | | | |

UNITED STATES PATENT AND TRADEMARK OFFICE
CERTIFICATE OF CORRRECTION

PATENT NO. : 5,853,397
DATED : December 29, 1998
INVENTOR(S) : Eli Shemesh, et. al.

It is certified that error appears in the above-identified patent and that said Letters Patent is hereby corrected as shown below:

Title page, item [56], insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | EP | 03 | 9 | 8 | 5 | 8 | 3 | 11/1990 | EP | | | | |
| | | EP | 02 | 7 | 3 | 7 | 1 | 4 | 7/1988 | EP | | | | |
| | | FR | 23 | 3 | 8 | 7 | 1 | 0 | 7/1977 | FR | | | | |
| | | DE | 41 | 2 | 6 | 0 | 8 | 8 | 1/1993 | DE | | | | |
| | | DE | 30 | 3 | 5 | 7 | 4 | 8 | 5/1982 | DE | | | | |

Signed and Sealed this

Sixth Day of April, 1999

Attest:

Attesting Officer

Q. TODD DICKINSON

Acting Commissioner of Patents and Trademarks